United States Patent [19]

Aoki et al.

[11] 4,080,464
[45] Mar. 21, 1978

[54] CERTAIN 3,4-DICHLOROPYRROLE-2,5-DIONE FUNGICIDES

[75] Inventors: Katsumichi Aoki; Hideo Arabori; Keigo Satake; Shiro Yamazaki, all of Iwaki, Japan

[73] Assignee: Kureha Kagaku Kogyo Kabushiki Kaisha, Tokyo, Japan

[21] Appl. No.: 592,299

[22] Filed: Jul. 1, 1975

[30] Foreign Application Priority Data

Jul. 1, 1974 Japan .................................. 49-74252
Oct. 21, 1974 Japan .................................. 49-120260

[51] Int. Cl.² .............................................. A01N 9/22
[52] U.S. Cl. ........................... 424/274; 260/326.5 FM
[58] Field of Search .............. 260/326.5 FM; 424/274

[56] References Cited

U.S. PATENT DOCUMENTS 2,726,981 12/1955 Wolf et al. .................. 260/326.5 FM 3,745,170 7/1973 Fujinami et al. .......... 210/326.5 FM

FOREIGN PATENT DOCUMENTS 1,174,372 12/1969 United Kingdom ...... 260/326.5 FM

Primary Examiner—V. D. Turner
Attorney, Agent, or Firm—Sughrue, Rothwell, Mion, Zinn and Macpeak

[57] ABSTRACT

A novel fungicidal composition for agricultural use is proposed. It has as the effective substance at least a member selected from the group defined by the following general formula:

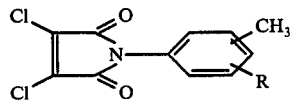

wherein
R stands for methyl or chlorine atom.

13 Claims, No Drawings

CERTAIN 3,4-DICHLOROPYRROLE-2,5-DIONE FUNGICIDES

This invention relates to a novel agricultural fungicidal composition having its effective substance of the type shown in the general formula:

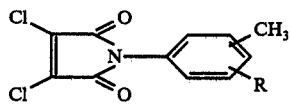

wherein
R stands for methyl or chlorine atom.

In recent decades, there has been made a remarkable progress in the field of agricultural fungicides. Various and novel compounds usable in this field have been found and practically utilized, resulting in a substantial reduction of plant diseases. However, there are yet numerous plant diseases to which easily usable convenient agricultural medicines have not yet been found. In addition, appearance of powerful and durable fungi to commonly used agricultural fungicides have been reported.

On the other hand, there is a strong desire towards an agricultural medicine which is usable to several different kinds of diseases of one and the same plant for elevating the agricultural productivity thereof. It is also a strong desire among those skilled in the art to develop a unique agricultural medicine which is applicable to various plants to control numerous and different agricultural diseases caused by fungi.

It is the main object of the present invention to provide a group of fungicidal agricultural medicines effectively controllable of blasts on rice plants; powdery mildew, downy mildew, phytophthora rot, gray mold, sclerotinia rot and the like on various useful vegetables and fruit trees such as cucumber, egg plant, strawberry, tomato, wheat, cabbage, onion, potato, soybean, kidney bean, apple tree, grape tree, common hop and the like, with superior effect.

Samples of the effective substances according to this invention, as grouped by the above general formula are as follows.

| Comp. No. | Structure | Nomination | m.p., °C |
|---|---|---|---|
| 1 | 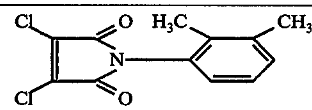 | 1-(2,3-dimethylphenyl)-3,4-dichloropyrrole-2,5-dione | 170–171 |
| 2 | 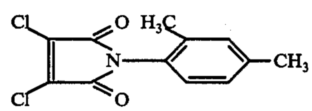 | 1-(2,4-dimethylphenyl)-3,4-dichloropyrrole-2,5-dione | 115–119 |
| 3 | 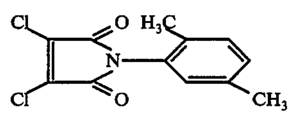 | 1-(2,5-dimethylphenyl)-3,4-dichloropyrrole-2,5-dione | 139–140 |
| 4 | 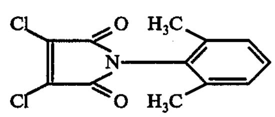 | 1-(2,6-dimethylphenyl)-3,4-dichloropyrrole-2,5-dione | 141–142 |
| 5 | 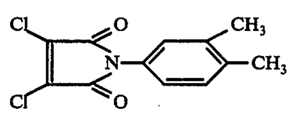 | 1-(3,4-dimethylphenyl)-3,4-dichloropyrrole-2,5-dione | 144–145 |
| 6 | 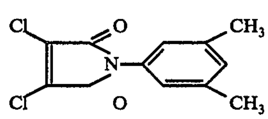 | 1-(3,5-dimethylphenyl)-3,4-dichloropyrrole-2,5-dione | 118–119 |
| 7 | 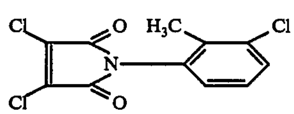 | 1-(3-chloro-2-methylphenyl)-3,4-dichloropyrrole-2,5-dione | 177–178 |
| 8 | 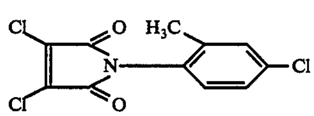 | 1-(4-chloro-2-methylphenyl)-3,4-dichloropyrrole-2,5-dione | 135.5–138 |
| 9 | 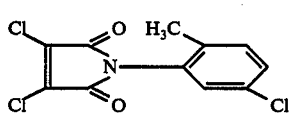 | 1-(5-chloro-2-methylphenyl)-3,4-dichloropyrrole-2,5-dione | 160–161.5 |

-continued

| Comp. No. | Structure | Nomination | m.p., °C |
|---|---|---|---|
| 10 | 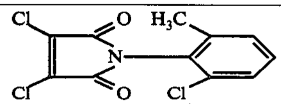 | 1-(6-chloro-2-methyl-phenyl)-3,4-dichloro-pyrrole-2,5-dione | 123.5–126.5 |
| 11 | 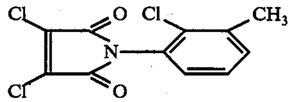 | 1-(2-chloro-3-methyl-phenyl)-3,4-dichloro-pyrrole-2,5-dione | 157–162.5 |
| 12 | 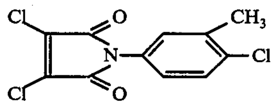 | 1-(4-chloro-3-methyl-phenyl)-3,4-dichloro-pyrrole-2,5-dione | 186.5–188 |
| 13 | 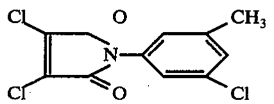 | 1-(5-chloro-3-methyl-phenyl)-3,4-dichloro-pyrrole-2,5-dione | 126.5–128.5 |
| 14 | 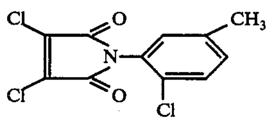 | 1-(6-chloro-3-methyl-phenyl)-3,4-dichloro-pyrrole-2,5-dione | 137.5–140.5 |
| 15 | 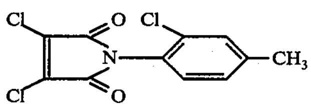 | 1-(2-chloro-4-methyl-phenyl)-3,4-dichloro-pyrrole-2,5-dione | 141–143 |
| 16 | 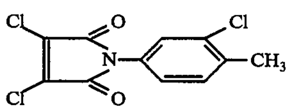 | 1-(3-chloro-4-methyl-phenyl)-3,4-dichloro-pyrrole-2,5-dione | 187.5–190 |

In the following, two examples of the synthetic preparation of the effective substances usable in this invention will be given by way of example of the above compounds No. 1 and 7, respectively.

EXAMPLE 1

(preparation of compound 1)

5 g of 2,3-dichloromaleic anhydride and 3.6 g of 2,3-xylidine were introduced in 100 ml of acetic acid and heated for 2 hours under strong agitation.

Acetic acid was distilled off from the reaction liquid and the residue was recrystallized from ethanol. 6.8 g of the desired product were obtained. Yield 84%. m.p. 170° – 171° C. It showed specific carbonyl absorptions to 3,4-dichloropyrrole-2,5-dione at 5.5 and 5.75 $\mu$ on IR, respectively.

EXAMPLE 2

(preparation of compound 7)

5 g of 2,3-dichloromaleic acid anhydride, 5.3 g of 3-chloro-2-methylaniline hydrochloride and 4.1 g of sodium acetate were heated in 100 ml of acetic acid for 2 hours. Acetic acid was distilled off from the reaction mixture and the residue was recrystallized from ethanol. 4.0 g of the desired product were obtained. Yield 52%. m.p. 177° – 178° C. Specific carbonyl absorptions to 3,4-dichloropyrrole-2,5-dione appeared at 5.5 and 5.75 $\mu$ on IR.

These compounds are usable per se or in the form of a mixture with a carrier or diluting substance and in any suitable state such as a dust, emulsifiable concentrate or sprayable liquid.

If necessary, the effective substance may be added with properly selected spreader, emulsifier, wetting substance, adhesive or the like additives for improving the using effect.

In the following, several recommended usable dosages will be given. However, these may be varied in broad range as the occasion may desire. The parts are shown by weight.

Usable dosage 1 (dust)

Compound No. 1 . . . 3 parts;
clay . . . 40 parts;
talc . . . 57 parts.

These are well mixed together and pulverized to a degree ready for practical use.

Usable dosage 2 (wettable powder)

Compound No. 5 . . . 50 parts;
polyoxyethylene alkylaryl ether . . . 6 parts;
kieselguhr . . . 44 parts.

These are well mixed together and pulverized to a wettable powder which may be used when combined with a properly diluting amount of water.

In the following, several experimental results for control of plant diseases caused by fungi are set forth, for showing the superior results of the inventive composition.

PLANT DISEASE CONTROL TEST EXPERIMENT 1

(pot tests on rice blast control)

A number of porous biscuit planting pots were planted with rice plants, Oryza sativa L, of four-leaf stage (variety: "Sasanishiki") and the plants were applied with the wettable powder prepared in accordance with the foregoing second dosage example and upon diluted with a proper amount of water to such a degree that an even suspension liquid was provided. This liquid suspension was applied to the rice plants to such a degree that all the leaves thereof were adequately wetted.

Upon drying, the leaves were inoculated with spores of the fungi causing rice blast disease, in the form of an aqueous suspension by spraying. Upon inoculation, the rice plants were preserved at 27° – 28° C and in a high humidity atmosphere. After a lapse of 4 days after inoculation, the affected spots on the leaves were counted as per top leaf per rice plant, 20 plants per pot and three pots per treatment and then, the control efficiency or more precisely inhibition percentage was determined from the following formula: Inh. percentage equals to (nu - nt) divided by nu and multiplied by 100.

where "nt" means total number of lesions on the treated leaves.

"nu" stands for total number of lesions on the untreated leaves.

The thus determined results are shown in the following tables 1 and 2.

Table 1

| Compound | ppm | Total lesions | Inh. perc. |
|---|---|---|---|
| No. 1 | 550 | 0 | 100 |
| No. 2 | " | 0 | 100 |
| No. 3 | " | 2 | 99.7 |
| No. 4 | " | 0 | 100 |
| No. 5 | " | 3 | 99.6 |
| No. 6 | " | 0 | 100 |
| Ref. "Kitazin-p" | 480 | 1 | 99.9 |
| control (untreated) | — | 759 | — |

In these tests, practically no phytotoxity was observed. "Kitazin-p" is a trade name of O,O-diisopropyl-S-benzylthio phosphate prepared and sold by "Kumiai Kagaku Kogyo K.K., Tokyo, being sold in the form of an emulsion, the concentration being 48%.

Table 2

| Comp. No. | ppm | Total lesions | Inh. perc. |
|---|---|---|---|
| 7 | 500 | 2 | 99.8 |
| 8 | " | 4 | 99.5 |
| 9 | " | 1 | 99.9 |
| 10 | " | 11 | 98.7 |
| 11 | " | 0 | 100 |
| 12 | 500 | 0 | 100 |
| 13 | " | 0 | 100 |
| 14 | " | 2 | 99.8 |
| 15 | " | 3 | 99.6 |
| 16 | " | 0 | 100 |
| "Kitazin-p" | 480 | 31 | 96.5 |
| Control (untreated) | — | 876 | — |

PLANT DISEASE CONTROL TEST EXPERIMENT 2

(pot tests on powdery mildew of cucumbers)

A number of porous biscuit planting pots, each having a 10-cm diameter which fact is also applicable to those used in the foregoing experiment 1, were planted with cucumber plants. Sphaerotheca fulginea), of two-leaf stage (variety: "Sagami-Hanpaku") and the plants were applied with the wettable powder prepared in accordance with the foregoing second dosage example and after dilution with a proper quantity of water to such a degree that an even suspension liquid was provided. This liquid suspension was applied to the cucumber plants to such a degree that all the leaves thereof were adequately wetted. Each pot had a cucumber plant and three pots constituted a treatment group.

After drying, the leaves were inoculated with spores of the fungi causing the above plant disease, in the form of an aqueous suspension by spraying. Upon inoculation, these potted plants were preserved at a high temperature and in a high humidity atmosphere. After lapse of 7 days after inoculation, the affected spots or lesions were counted as per leaf per pot and per three pots per treatment, and the degree of affection was determined in the following classification.

| | Classification |
|---|---|
| "0" | unaffected. |
| "0.5" | affected leaf area less than 10 percent of the total inoculated leaf area. |
| "1" | affected leaf area lying between 10 – 20 percent of total inoculated leaf area. |
| "2" | between 20 – 40 percent. |
| "3" | between 40 – 60 percent. |
| "4" | between 60 – 80 percent. |
| "5" | over 80 percent. |

The test results are shown in the following tables 3 – 5.

Table 3

| Comp. No. | ppm | deg. of affection |
|---|---|---|
| 1 | 500 | none |
| 2 | " | " |
| 3 | " | " |
| 4 | " | " |
| 5 | " | " |
| 6 | " | " |
| "Morestan"(comparative) | 62.5 | " |
| untreated (as control) | — | 5 |

In all these tests, substantially no phytotoxicity was observed.

Table 4

| Comp. No. | ppm | deg. of affection |
|---|---|---|
| 7 | 300 | 0 |
| 8 | " | 0.5 |
| 9 | " | 0 |
| 10 | " | 0.5 |
| 11 | " | 0 |
| 12 | " | 0 |
| 13 | " | 0 |
| 14 | " | 0.5 |
| 15 | " | 0.5 |
| 16 | " | 0 |
| "Morestan"(comparative) | 125 | 0 |
| untreated as control | — | 5 |

"Morestan" stands for 6-methyl quinoxaline-2,3-dithiocarbonate and prepare and sold in form of a 25-percent wettable powder by a Japanese firm "Nippon Tokushu Noyaku Seizo K.K., Tokyo.

As in the similar way disclosed in the foregoing test experiment 2, pot tests were performed for determining the fungicidal effect on downy mildew (Pseudoperonospora cubensis) on cucumber.

Inoculated plants were preserved at 22° – 23° C in high humidity atmosphere for 24 hours and then at room temperature. Observation was made after 5 days upon inoculated. The results are shown in the following Table 5.

Table 5

| Comp. No. | ppm | mean deg. of affection |
|---|---|---|
| 1 | 500 | 0 |
| 2 | " | 0 |
| 3 | " | 0 |
| 4 | " | 0 |
| 5 | " | 0 |
| 6 | " | 0 |
| 7 | 300 | 0 |
| 8 | " | 0.5 |
| 9 | " | 1 |
| 10 | " | 0.5 |
| 11 | " | 1 |
| 12 | " | 0 |
| 13 | " | 0 |
| 14 | " | 0.5 |
| 15 | " | 0 |
| 16 | " | 0 |
| "Daconil"(comparative) | 750 | 0 |
| untreated (as control) | — | 5 |

In all these tests, practically no phytotoxicity was observed.

"Daconil" stands for tetrachloroisophthalonitrile and prepared and sold by a Japanese firm Takeda Pharmaceutical Company, Osaka, in form of a 75-percent wettable powder.

Plant Disease Control Test

Experiment 4 (pot tests on late blight of tomato (phytophthora infectans)

A number of porous biscuit planting pots, each being of 10 cm-diameter, were planted with tomato plants, Phytophthora infestans, of four leaf stage (variety: "Fukuju-No. 2", a plant per each pot, a treating group being constituted by three pots. These plants were applied with the wettable powder prepared in accordance with the foregoing second dosage example after dilution with a proper amount of water to such a degree that an even suspension liquid was provided. This liquid suspension was applied onto the tomato plants to such degree that all the leaves thereof were adequately wetted.

After drying, the leaves were inoculated with spores of the fungi causing late blight, in the form of an aqueous suspension spraying. The fungi had beforehand been cultured on potato tubers.

After inoculation, the tomato plants were preserved at 20 — 20 deg. C in a high humidity atmosphere, for two complete days and then at room temperature. After lapse of 4 days after inoculation, the affected areas on the leaves were examined as in the similar way to that disclosed in the foregoing test experiment 2. The observed results are shown in the following Table 6.

Table 6

| Comp. No. | ppm | deg. of affection |
|---|---|---|
| 1 | 50 | 0 |
| 2 | " | 0 |
| 3 | " | 0.5 |
| 4 | " | 0 |
| 5 | " | 0.5 |
| 6 | " | 0 |
| 7 | 500 | 0.5 |
| 8 | " | 0 |
| 9 | " | 1 |
| 10 | " | 0.5 |
| 11 | " | 1 |
| 12 | " | 0.5 |
| 13 | " | 0.5 |
| 14 | " | 0 |
| 15 | " | 0.5 |
| 6 | " | 0 |
| "Daconil"(comparative) | 750 | 0 |
| Untreated (as control) | — | 5 |

In these tests, practically no phytotoxicity was observed.

"Daconil" stands for tetrachloroisophthalonitrile which was prepared and sold by Takeda Pharmaceutical Company, Osaka, Japan, in the form of a 75% hydrated and wetted powder.

Plant Disease Control Test Experiment 5 (pot tests on gray mold of cucumber Botrytis cinerea)

A number of porous biscuit planting pots, each having a 10-cm diameter as before, were planted with cucumber plants, Botrytis cinerea of two-leaf stage, (variety: "Sagami-hanpaku") of two-leaf stage, one plant per pot, and the plants were applied with the wettable powder prepared in accordance with the foregoing second dosage example after dilution with a proper quantity of water to such a degree that an even suspension liquid was supplied. This liquid suspension was applied onto the cucumber plants to such degree that all the leaves thereof were adequately wetted.

After drying, the leaves were inoculated with spores of the fungi causing gray mold.

These fungi had been cultured on sugar-added potato extract agar at 20° C for 5 days. Then, the cultured agar were cut into small discs of 5 mm-diameter and then attached to the pre-treated cucumber leaves, being two discs per leave.

During 4 days after the inoculation, the cucumber plants were kept at 22° – 23° C and then, the degree of affection was determined for two leaves and thus four inoculated areas per plant in accordance with the following classification. The results are shown in the following Tables 7 and 8 and by observation of mean affected degree per one inoculated area.

| | Classification |
|---|---|
| "0" | unaffected. |
| "0.5" | affected area corresponding to agar disc or its proximity only. |
| "1" | affected less than 20 percent of leaf surface inoculated. |
| "2" | affected area corresponding to 20 – 40 percent. |
| "3" | 40 – 60 percent. |
| "4" | 60 – 80 percent. |
| "5" | over 80 percent. |

Table 7

| Comp. No. | ppm | mean affected degree |
|---|---|---|
| 1 | 500 | 0 |
| 2 | " | 0.5 |
| 3 | " | 0 |
| 4 | " | 0 |
| 5 | " | 0 |
| 6 | " | 0 |
| "Topsin-M"(comparative) | 700 | 0 |
| untreated (as control) | — | 5 |

In all these tests, practically no phytotoxicity was observed.

"Topsin-M" stands for 1,2-bis(3-methoxycarbonyl-2-thioureid)benzene which was prepared and sold by a Japanese firm "Nippon Soda K.K.," Tokyo, in the form of a 70-percent wettable powder.

Table 8

| Comp. No. | ppm | mean degr. of affection |
|---|---|---|
| 7 | 500 | 0 |
| 8 | " | 0 |
| 9 | " | 0.5 |
| 10 | " | 0.5 |

Table 8-continued

| Comp. No. | ppm | mean degr. of affection |
|---|---|---|
| 11 | " | 0 |
| 12 | " | 0 |
| 13 | " | 0 |
| 14 | " | 1 |
| 15 | " | 0 |
| 16 | " | 0 |
| "Sclex"(comparative) | 300 | 0 |
| untreated (as control) | — | 5 |

In these tests, no phototoxicity was practically observed.

"Sclex" stands for 3-(3,5-dichlorophenyl)-5,5-dimethyloxazolidinedione-2,4 which was prepared and sold by a Japanese firm "Hokko Kagaku Kogyo K.K.", in the form of a 30%-hydrated wettable powder.

Plant Disease Control Test Experiment 6 (pot tests on kidney bean plants for stem rot control)

A number of porous biscuit planting pots were planted with kidney bean plants, Sclerotinia screrotiorum, of three-leaf stage (variety: "Kintoki") and the plants were applied with the wettable powder prepared in accordance with the foregoing second dosage example after dilution with a proper amount of water to such a degree that an even suspension liquid was provided. This liquid suspension was applied to the plants to such degree that all the leaves were adequately wetted.

After drying, the leaves were inoculated with spores of the fungi causing the stem rot disease, in the form of an aqueous suspension by spraying. After inoculation, the plants were preserved at 22° - 23° C and in a high humidity atmosphere for 3 days.

These fungi had been cultured on sugar-added potato extract agar at 20° C for 5 days. The cultured agar was cut into small discs of 5 mm-diameter. The inoculation was carried out by direct attachment of two disc onto each leaf of the plants. After lapse of 3 days upon inoculation, two leaves or four inoculated areas per plant were investigated for the determination of the mean affected degree as before. The results are shown in the following Tables 9 and 10.

Table 9

| Comp. No. | ppm | deg. of mean affection |
|---|---|---|
| 1 | 500 | 0 |
| 2 | " | 0 |
| 3 | " | 0 |
| 4 | " | 0 |
| 5 | " | 0 |
| 6 | " | 0 |
| "Topsin-M"(comparative) | 700 | 0 |
| untreated (as control) | — | 5 |

In all these tests, no phytotoxicity was practically observed.

Table 10

| Comp. No. | ppm | degree of mean affection |
|---|---|---|
| 7 | 500 | 0 |
| 8 | " | 0.5 |
| 9 | " | 1 |
| 10 | " | 1 |
| 11 | " | 0.5 |
| 12 | " | 0 |
| 13 | " | 0 |
| 14 | " | 0.5 |
| 15 | " | 0 |
| 16 | " | 0 |
| "Sclex" | 300 | 0 |
| untreated | — | 5 |

In all these tests, no phytotoxicity was practically observed.

Plant Disease Control Test Experiment 7 (pot tests on downy mildew of vine plants)

Pots were used for culture of young vine trees, two-year age (variety: "Neo-muscut") and these potted plants were applied with the wettable powder prepared in accordance with the foregoing dosage example 2, after dilution with a proper quantity of water for wetting both surfaces of each of the vine leaves with the thus prepared liquid suspension.

After drying, spores of the fungi taken from other vine leaves affected with downy mildew and prepared into an aqueous suspension were inoculated onto the pretreated leaves by spraying. These plants were then preserved at 18° - 23° C in high humidity atmosphere in a specially designed preservation chamber.

Upon lapse of 10 days after inoculation, the degree of mean affection of the vine leaves was investigated for determination of the affected degree which was determined as the mean value per leaf and in accordance with the following classification:

| Class | Classification : Degree of Affection |
|---|---|
| "0" | unaffected |
| "1" | less than 25 percent affected area of total leaf area. |
| "2" | between 25 - 50 percent. |
| "3" | between 50 - 75 percent. |
| "4" | over 75 percent. |

The investigated test results are shown in the following Table 11.

Table 11

| Comp. No. | ppm | deg. of affection |
|---|---|---|
| 1 | 1000 | 1 |
| 2 | " | 3 |
| 4 | " | 2 |
| 5 | " | 1 |
| 7 | " | 1 |
| 12 | " | 1 |
| 13 | " | 1 |
| 16 | " | 1 |
| untreated | — | 4 |

TEXT EXPERIMENT 8

(field tests on powdery mildew of vine trees - Uncinula necator)

Three matured vine trees (variety: "Koshu") on a field were tested. The wettable powder suspension as used in the foregoing test experiments was sprayed four times (June 14th, 21st, July 1st and 15th) onto the leaves of these vine trees. The sprayed quantity was 250 lit. per 10 acres. Investigation was made August 10th of the same year by taking out 40 leaves at random from each tree. The degree of affection was determined by counting the affected leaves. The results are shown in the following Table 12.

Table 12

| Comp. No. | concent. ppm | observed leaves | mean affected leaves | percentage of affected leaves |
|---|---|---|---|---|
| 1 | 1,000 | 40 × 3 trees | 9.7 | 24.2 |
| 2 | " | " | 18.3 | 45.8 |
| 5 | " | " | 6.3 | 15.7 |
| 7 | " | " | 9.3 | 23.2 |
| 11 | " | " | 7.3 | 18.2 |
| 13 | " | " | 12.7 | 31.8 |

Table 12-continued

| Comp. No. | concent. ppm | observed leaves | mean affected leaves | percentage of affected leaves |
|---|---|---|---|---|
| untreated | — | " | 36.6 | 91.5 |

The embodiments of the invention in which an exclusive property or privilege is claimed are as follows:

1. A fungicidal composition for agricultural use, comprising a carrier and a fungicidally effective amount of a compound of the formula:

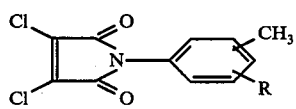

wherein

R stands for methyl or chlorine atom.

2. The composition of claim 1 wherein the compound is 1-(2,3-dimethylphenyl)-3,4-dichloropyrrole-2,5-dione.

3. The composition of claim 1 wherein the compound is 1-(2,4-dimethylphenyl)-3,4-dichloropyrrole-2,5-dione.

4. The composition of claim 1 wherein the compound is 1-(2,5-dimethylphenyl)-3,4-dichloropyrrole-2,5-dione.

5. The composition of claim 1 wherein the compound is 1-(3,5-dimethylphenyl)-3,4-dichloropyrrole-2,5-dione.

6. The composition of claim 1 wherein the compound is 1-(3-chloro-2-methylphenyl)-3,4-dichloropyrrole-2,5-dione.

7. The composition of claim 1 wherein the compound is 1-(4-chloro-2-methylphenyl)-3-4-dichloropyrrole-2,5-dione.

8. The composition of claim 1 wherein the compound is 1-(5-chloro-2-methylphenyl)-3,4-dichloropyrrole-2,5-dione.

9. The composition of claim 1 wherein the compound is 1-(6-chloro-2-methylphenyl)-3,4-dichloropyrrole-2,5-dione.

10. The composition of claim 1 wherein the compound is 1-(2-chloro-3-methylphenyl)-3,4-dichloropyrrole-2,5-dione.

11. The composition of claim 1 wherein the compound is 1-(5-chloro-3-methylphenyl)-3,4-dichloropyrrole-2,5-dione.

12. The composition of claim 1 wherein the compound is 1-(6-chloro-3-methylphenyl)-3,4-dichloropyrrole-2,5-dione.

13. The composition of claim 1 wherein the compound is 1-(3-chloro-4-methylphenyl)-3,4-dichloropyrrole-2,5-dione.

* * * * *